(12) United States Patent
Johnson et al.

(10) Patent No.: US 10,182,792 B2
(45) Date of Patent: Jan. 22, 2019

(54) PROBE TIP ASSEMBLY AND METHOD OF USING SAME

(71) Applicant: SonaCare Medical, LLC, Charlotte, NC (US)

(72) Inventors: Christie Johnson, Avon, IN (US); Adam Morris, Camden, IN (US); Mark Carol, Charlotte, NC (US); Narendra Sanghvi, Indianapolis, IN (US); Jacob Carr, Indianapolis, IN (US)

(73) Assignee: SonaCare Medical, LLC, Charlotte, NC (US)

( * ) Notice: Subject to any disclaimer, the term of this patent is extended or adjusted under 35 U.S.C. 154(b) by 813 days.

(21) Appl. No.: 14/191,593

(22) Filed: Feb. 27, 2014

(65) Prior Publication Data

US 2014/0243677 A1 Aug. 28, 2014

Related U.S. Application Data

(60) Provisional application No. 61/769,811, filed on Feb. 27, 2013.

(51) Int. Cl.
| | |
|---|---|
| *A61B 8/12* | (2006.01) |
| *A61B 8/00* | (2006.01) |
| *A61N 7/02* | (2006.01) |
| *A61B 46/10* | (2016.01) |
| *A61B 18/00* | (2006.01) |
| *A61N 7/00* | (2006.01) |

(52) U.S. Cl.
CPC .......... *A61B 8/4444* (2013.01); *A61B 8/4281* (2013.01); *A61B 46/10* (2016.02); *A61N 7/022* (2013.01); *A61B 2018/00023* (2013.01); *A61N 2007/0052* (2013.01); *A61N 2007/0065* (2013.01)

(58) Field of Classification Search
CPC .................................. A61B 8/12; A61B 8/445
See application file for complete search history.

(56) References Cited

U.S. PATENT DOCUMENTS

| | | | | |
|---|---|---|---|---|
| 5,372,138 | A * | 12/1994 | Crowley | A61B 5/416 600/463 |
| 5,817,015 | A * | 10/1998 | Adair | A61B 1/00101 600/121 |
| 8,038,631 | B1 * | 10/2011 | Sanghvi | A61N 7/022 600/439 |
| 2007/0142711 | A1 * | 6/2007 | Bayer | A61B 1/00016 600/175 |
| 2007/0167813 | A1 * | 7/2007 | Lee | A61B 8/12 600/459 |
| 2009/0192445 | A1 * | 7/2009 | Jessen | A61B 5/14528 604/27 |

(Continued)

*Primary Examiner* — Patricia J Park
(74) *Attorney, Agent, or Firm* — Mark T. Vogelbacker; Eckert Seamans Cherin & Mellott, LLC

(57) ABSTRACT

A probe tip assembly for receiving at least a portion of an ultrasound probe therein includes a body having a proximal end and an opposing distal end. A first opening may be located at the proximal end of the body. The first opening may be sized and shaped to receive at least a portion of the probe therein. A second opening may be proximate the distal end of the body. A membrane may cover the second opening.

14 Claims, 6 Drawing Sheets

(56) References Cited

U.S. PATENT DOCUMENTS

2010/0286791 A1* 11/2010 Goldsmith ....... A61B 17/12022
              623/23.7
2013/0247921 A1*  9/2013 Dye ..................... A61B 46/23
              128/853

* cited by examiner

PROBE TIP ASSEMBLY AND METHOD OF USING SAME

CROSS-REFERENCE TO RELATED APPLICATIONS

The present application claims priority to U.S. Provisional Application No. 61/769,811, entitled "PROBE TIP ASSEMBLY" and filed on Feb. 27, 2013, which is herein incorporated by reference in its entirety.

BACKGROUND

Among the technologies being considered, developed or currently deployed for use in treating abnormalities of human and animal tissue is focused ultrasound (FU). Focused ultrasound devices use ultrasound transducers to deliver generally thermal or cavitational dose to a small, well-defined spot at some fixed or focal distance from the transducer surface. Typically, the region to be treated is larger than the small spot of dose that is delivered from the transducer.

One way to deliver thermal dose to a larger region is to move the transducer so that the small spot of thermal dose is scanned over the region that is to receive thermal or cavitational dose. Another way is to move the patient relative to the transducer. The latter approach is often used in extracorporeal devices where the transducer is located outside the patient. Such is the case with the EXABLATE system. The former approach is used often in devices where the transducer is located inside the patient. Such is the case with devices such as the Sonatherm and SONABLATE devices.

In devices where the transducer is introduced into the patient and is moved potentially relative to the patient, it is typically deployed in a probe. Typically, such probes include an acoustic window for passage of the FU and a way to coupling the acoustic window to the tissue to be treated. Coupling involves providing a continuous acoustic path between the transducer and the tissue being treated. The coupling mechanism, typically degassed water, is contained by an acoustically invisible membrane made typically of materials such as latex. The acoustic window, through which the FU will pass, and its coupling mechanism are brought in contact with the tissue through which the FU will pass. The coupling mechanism also is used as a spacing device in order to position the focal post of the transducer the correct distance from tissue. By increasing the volume of coupling fluid contained within the membrane, the tissue can be pushed further from the transducer. Finally, the fluid used in the coupling mechanism can be circulated around the transducer in order to remove heat buildup from around the transducer or even to increase the temperature of the transducer. Cooling can have a protective effect on tissue against which the probe is brought, removing excess heat delivered to tissue directly adjacent to the probe if that tissue is not to be part of the region being treatment (heated). Conversely, heated fluid can be used to increase the amount of heat retained by the tissue if it is to be included in the planned treatment.

In instances where the probe is introduced into a sterile environment, the portion of the probe that comes in contact with tissue should be sterile. The water used to provide the coupling mechanism also should be sterile. There also are instances where the probe is introduced into a nonsterile environment, such as the rectum for transrectal ablation of the prostate, and where contamination of the water path, and therefore anything that comes in contact with the water used in the water path, is possible.

Ultrasound probes also are used for imaging purposes. In such an application, an ultrasound transducer mounted inside a probe is surrounded by a tissue coupling medium in order to provide an acoustic path to the tissue being imaged. This tissue coupling medium may be internal to the probe housing in direct contact with the transducer and/or may be applied to the surface of the probe in the form of a gel or contact medium.

BRIEF SUMMARY

Providing a sterile probe, whether imaging or therapy or both, can be difficult. For example, with most existing probe designs, where the entire system is provided as a single unit, it may be difficult or impossible to find a way to sterilize the entire probe, due specifically to the physical size of the probe. In addition, many cables, electrical circuits and electro-mechanical components may not be suitable to a sterilization process. This is especially the case in countries outside the U.S., where sterilization options are limited and when available tend to run on the smaller size.

Another potential difficulty is related to the membrane used typically to contain the tissue coupling medium. Commercial condoms are often used, placed over the probe, because they can be supplied sterile and they are elastic, allowing the fluid coupling distance to be increased/decreased to meet the specific needs of a treatment. However, the condoms may break or rupture when snagged on a surgical instrument, require manipulation in order to stretch and provide delivery over the probe head, and require (a secondary) o-ring(s) to secure them to the probe itself in order to prevent fluid escaping into the patient.

An additional disadvantage of the prior art is related to the fluid path required to support the tissue coupling mechanism and to provide transducer coupling. Typically, this fluid path is provided internal to the probe itself, making for a compact and self-contained delivery device. However, it can become difficult to clean and sterilize this path as the tubes are small and located internal to electronic components that cannot be steam sterilized or soaked in disinfectant.

A further disadvantage related to such a system is the need to cover the probe with a sterile drape in order to protect the sterile field of operation. Typically, this requires the use of clear or opaque drape that comes prepackaged sterile, which is placed around or over the exposed portions of the probe that may not be sterile. This process is prone to creating regions that are not covered. It also can be difficult to mate the drape to or cover portions of the probe that are introduced into the patient.

Where the probe is used in an environment where it can become contaminated, a problem can arise if the water comes in contact with portions of the probe that may be hard or impossible to disinfect. For instance, in transrectal FU treatments, it is possible for the membrane used to create the means of tissue coupling and the means of probe cooling to rupture, thereby exposing the region inside the membrane to fecal material. In current system designs, where the water path in internal to the probe itself, fecal material could be brought in contact with the internal workings of the probe that might be very hard to clean.

Regardless of whether an ultrasound probe is used in a sterile or non-sterile environment or for imaging or therapy, if fluid is used to surround the transducer, that fluid should be bubble-free. Bubbles can disrupt the delivery of ultrasound energy into the tissue; their presence can produce erroneous imaging data or incorrectly delivered therapeutic treatments. The removal of bubbles can be a time consuming and frustrating experience involving manipulating the probe so that any bubbles in the system "rise" to some location where there is a means to let them vent out of the fluid path.

Thus, there is a need for an approach to focused therapeutic ultrasound probe design that provides a fluid coupling and fluid cooling mechanism that can be used satisfactorily in a sterile environment or in an environment that is desired to be bubble free. The device, system and method of the present disclosure satisfy the above and other objectives.

In one embodiment of the present disclosure, a probe tip is provided for an ultrasound probe which may include an integrated means for introducing and removing fluid from within the probe tip, an integrated tissue coupling mechanism, and a means for quickly and reliably securing the probe tip to the probe body in the desired orientation such that the acoustic window and tissue coupling mechanism provided by the probe tip aligns correctly with the transducer in at least two planes or axes of the transducer A probe tip assembly of the present disclosure may have multiple functions incorporated into its design including: Luer fittings for direct connection of a water circulatory system; a water reservoir for coupling of high frequency sound for both ablative therapy and imaging through the water path and membrane into tissue to be treated; a sealing surface to seal the water circulation into the tip and act as a rigid surface for the seal to act as a compression spring in order to engage the locking mechanism to the probe body; and locking tabs that are different sizes that allow the tip to be placed only onto the body in one manner so that the acoustic window/membrane is aligned with the radiating face of the ultrasound transducer.

In one embodiment of the present disclosure, a disposable probe tip, which may be placed over a focused ultrasound transducer, is provided in a sterile package to be placed over the nonsterile transducer portion of the probe, thereby creating a tissue coupling mechanism and providing a sterile water path.

In an additional embodiment of the present disclosure, a disposable probe tip, which may be placed over a focused ultrasound transducer, is provided with a sterile tube drape integrated into the proximal end of the probe tip, such that the tube drape can be unrolled over the nonsterile portion of the probe after the probe tip is placed over the transducer thereby creating a seamless sterile barrier.

In another embodiment of the present disclosure, a disposable probe tip, including an acoustic window and a tissue coupling mechanism to be placed over a focused ultrasound transducer, is provided with inflow and outflow ports that can be connected to a water supply system controlled by a pump such that fluid can be actively passed through the probe tip, thereby creating a means for cooling or heating the transducer and or the tissue against which the tissue coupling mechanism is brought to bear.

In a further embodiment of the present disclosure, the acoustic coupling may be seamlessly bonded inside the probe tip so that transducer can easily traverse in both longitudinal and transverse planes to provide tissue imaging and treatment with ultrasound energy in two orthogonal planes to the transducer axis and so that it can pass through a trocar or other body cavity without friction.

In a further embodiment of the present disclosure, a disposable probe tip, which may be placed over a focused ultrasound transducer, is designed to be used in a nonsterile environment to provide a reliable tissue coupling mechanism, as well as a separate and distinct water path, whereby the water does not come in contact with any mechanisms internal to the probe itself.

In a further embodiment of the present disclosure, a disposable probe tip to be placed over an imaging ultrasound transducer is designed to be used in a sterile or nonsterile environment, whereby the tissue up against which the probe is placed can be cooled or warmed actively if desired as a result of fluid passing through the probe tip.

In an additional embodiment of the present disclosure, a disposable probe tip to be placed over a focused ultrasound transducer may include a controllable air vent, wherein at least some or all air bubbles can be removed from the fluid filling the probe tip and surrounding the enclosed transducer as the water is flowing into and filling the region surrounding the enclosed transducer.

In one aspect of the present disclosure, a method of delivering focused therapeutic ultrasound includes: passing a sterile probe tip assembly with an acoustic window surrounded by a tissue coupling mechanism over an ultrasound transducer, securing the probe tip to the body of the probe such that the acoustic window and tissue coupling mechanism is aligned correctly relative to the transducer, connecting water lines to the probe tip, introducing the probe in a sterile manner into a patient, circulating sterile water into the probe tip to cool or heat the transducer and/or the tissue as desired, such that the tissue coupling mechanism is brought to make air-free contact to tissue, and using the sterile water to increase or decrease the size of the coupling mechanism so as to bring the transducer to the proper position relative to tissue and transmit correctly ultrasound energy to or through the sterile tissue against which it has been positioned.

In an additional aspect of the present disclosure, a method of delivering focused therapeutic ultrasound includes: passing a sterile probe tip assembly with an acoustic window surrounded by a tissue coupling mechanism over an ultrasound transducer, securing the probe tip to the body of the probe such that the acoustic window and tissue coupling mechanism is aligned correctly relative to the transducer window, connecting water lines to the probe tip, unrolling an integrated tube drape attached to the proximal end of the probe tip over the probe body, introducing the probe in a sterile manner into a patient, circulating water into the probe tip to cool or heat the transducer and/or the tissue against which the tissue coupling mechanism is brought to bear if desired, and using the water to increase or decrease the size of the tissue coupling mechanism so as to bring the transducer to the proper position relative to sterile tissue and transmit correctly ultrasound energy to or through the sterile tissue against which it has been approximated.

In another aspect of the present disclosure, a method of delivering focused therapeutic ultrasound includes: passing a probe tip assembly with an acoustic window surrounded by a tissue coupling mechanism over an ultrasound transducer, securing the probe tip to the body of the probe such that the acoustic window and tissue coupling mechanism is aligned correctly relative to the transducer window, connecting water lines to the probe tip, introducing the probe in a non-sterile manner into a patient, circulating water into the probe tip to cool or heat the transducer and/or the tissue against which the tissue coupling mechanism is brought to bear if desired, and using the water to increase or decrease the size of the tissue coupling mechanism so as to bring the transducer to the proper position relative to tissue and transmit correctly ultrasound energy to or through the tissue against which it has been approximated.

In a further aspect of the present disclosure, a method of delivering focused therapeutic ultrasound includes opening an air valve at the distal end of the probe tip, holding the probe in the vertical position, allowing water to flow into the probe tip, then closing the air vent once all or substantially all air has been removed from the system.

DETAILED DESCRIPTION OF THE PRESENT DISCLOSURE

Figure 1:
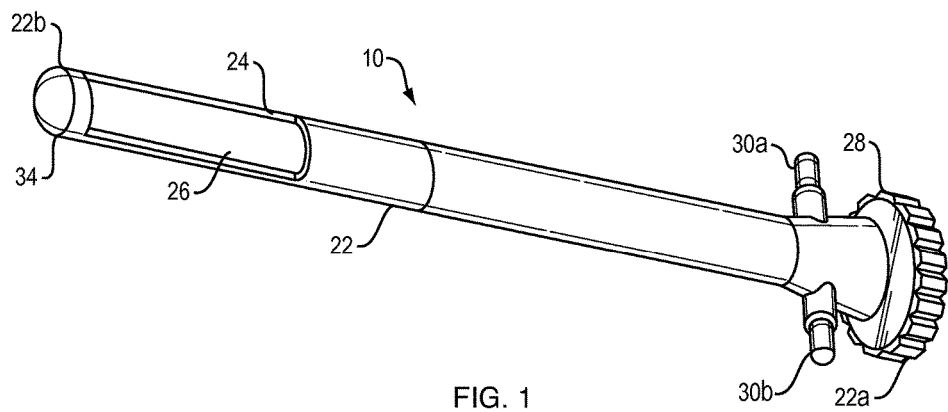
FIG. 1 is a perspective view of a probe tip assembly according to an embodiment of the present disclosure.

Various embodiments of the present disclosure are described hereinafter with reference to the figures. It should be noted that the figures are not drawn to scale and elements of similar structures or functions are represented by like reference numerals throughout the figures. It should also be noted that the figures are not intended to facilitate the description of specific embodiments of the present disclosure. The figures are not intended as an exhaustive depiction or description of the present disclosure, or a limitation on the scope of the present disclosure. In addition, an aspect described in conjunction with a particular embodiment of the present disclosure is not necessarily limited to that embodiment and may be practiced in any other embodiments of the present disclosure. It will be appreciated that while various embodiments of the present disclosure are described in connection with radiation treatment of tumors, the claimed disclosure has application in other industries and to targets other than cancers. Embodiments of the present disclosures, as depicted in FIG. 1, include a probe tip assembly, generally designated 10, designed to be used in conjunction with and/or connect to an ultrasound (US) probe, generally designated 12, (see FIGS. 2 and 3). The probe 12 is used to generate diagnostic images and/or to deliver a therapeutic dose of focused ultrasound that will heat and/or disrupt tissue either permanently or transiently.

The phrase "focused therapeutic ultrasound" is broadly defined herein as, for example, low intensity focused ultrasound, pulsed high intensity and continuous high intensity focused ultrasound, and/or non-thermal or cavitational focused ultrasound. The foregoing is not intended to exclude the case where focused ultrasound is used in an imaging mode.

Figure 2:
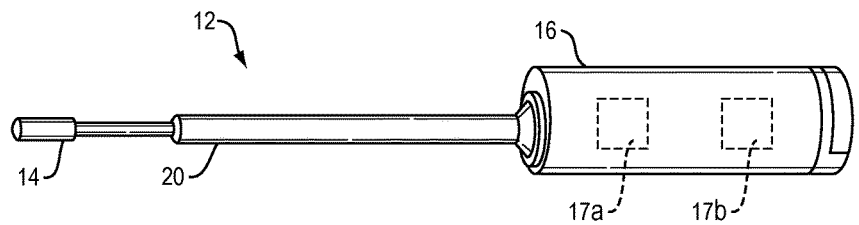
FIG. 2 is a perspective view of an ultrasound (US) probe.
Figure 3:
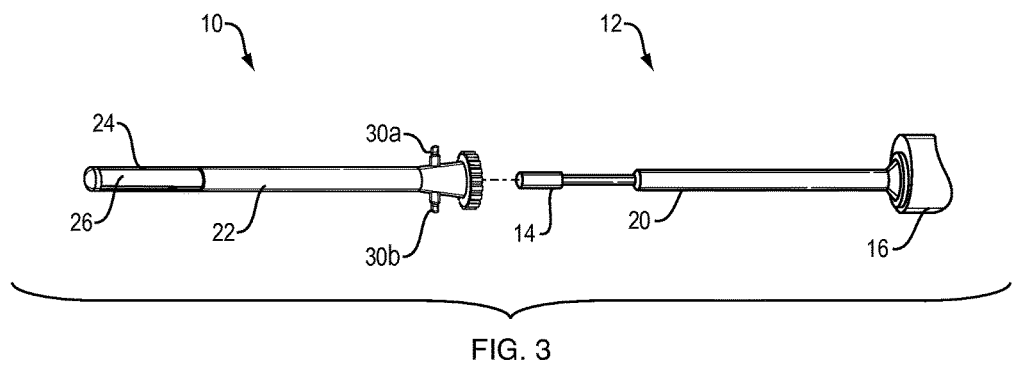
FIG. 3 is a perspective view of the probe tip assembly shown in FIG. 1 in relation to a portion of the probe shown in FIG. 2.

As shown in FIGS. 2 and 3, the probe 12 may include an ultrasound transducer 14 connected to a probe housing 16. The probe housing 16 may contain electronics 17a and one or more motors 17b (shown in broken lines in FIG. 2). The electronics 17a and motors 17b may be used to operate and/or manipulate portions of the probe 12 by a shaft 20. In particular, the shaft 20 may be used to move the transducer 14 in space relative to the probe housing 16. The transducer 14 may lie in a known linear and/or rotational position relative to the probe housing 16.

In one embodiment, the probe tip assembly 10 includes a body 22 having a proximal end 22a and an opposing distal end 22b (see FIG. 1). The proximal end 22a of the body 22 may include an opening or passageway to receive at least a portion of the probe 12 therein. A second opening or window 24, which may be covered with an acoustically transparent elastic membrane 26, may be positioned at or near the distal end 22b of the body 22. The body 22 may be formed of an injection molded or cast rigid plastic, and may define or surround a cavity for receiving at least a portion of the probe 12 therein. However, the body 22 may be formed by other methods and of other materials. The membrane 26 can be pre-formed through dip, cast, blow or injection molding; or formed in place through an over-mold process to become a seamless integral part of the probe tip assembly 10. If pre-formed, the membrane 26 may be bonded in place using an adhesive. All materials may be USP Class VI, ISO 10993, and can be sterilized prior to use.

The probe tip assembly 10 may be of a shape, size and/or configuration determined by the shape, size and/or configuration of the transducer 14, the shaft 20 and/or the probe housing 16. As shown in FIGS. 1, 3, 5 and 6, the window 24 may have at least a generally linear or rectangular shape. A length of the acoustic window 24, as measured parallel to a longitudinal axis of the probe tip assembly 10 (see FIG. 7), may be determined by the distance the transducer 14 will travel in order to image and/or treat tissue. At least a portion of the membrane 26, such as an outer periphery thereof, may be secured or attached to an inside or outside of the body 22 of the probe tip assembly 10. The acoustic membrane 26 may be made of a material that retains its shape, yet can balloon outwardly from the body 22 a known or predetermined amount under a given amount of applied internal pressure.

Referring to FIGS. 4, 7 and 11-13, at the proximal end 22a thereof, the probe tip assembly 10 may include a mechanism 28 that may both secure the probe tip assembly 10 to the probe housing 16 and secure the probe tip assembly 10 in an orientation that will align the acoustic window 24 of the probe tip assembly 10 with the transducer 14. Alternatively, the probe 12 may include the entire mechanism 28 or only a portion of the mechanism 28. The mechanism 28 may include one or more openings, undercuts and/or grooves, which may allow the probe tip assembly 10 to be engaged with, seal and/or capture at least a portion of the probe 12.

Figure 11:
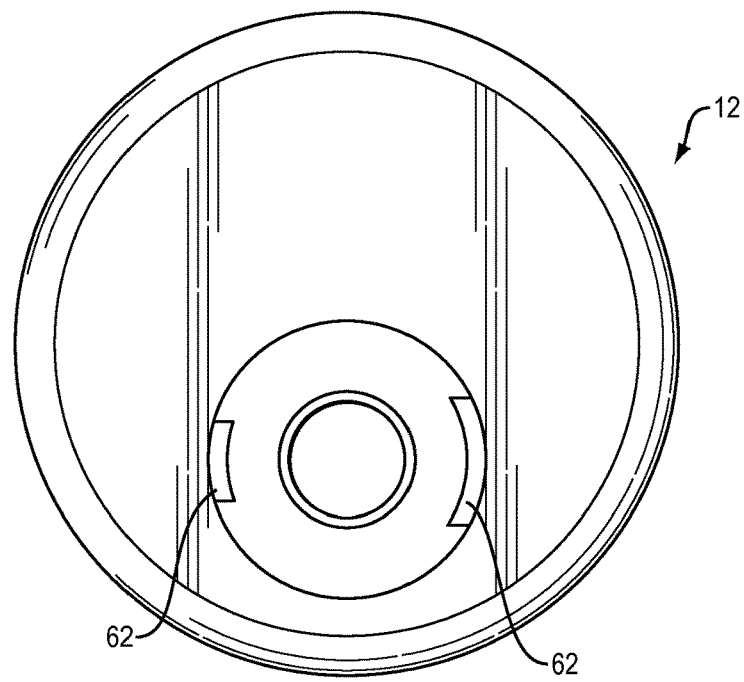
FIG. 11 is a front elevation view of at least a portion of the probe.
Figure 12:
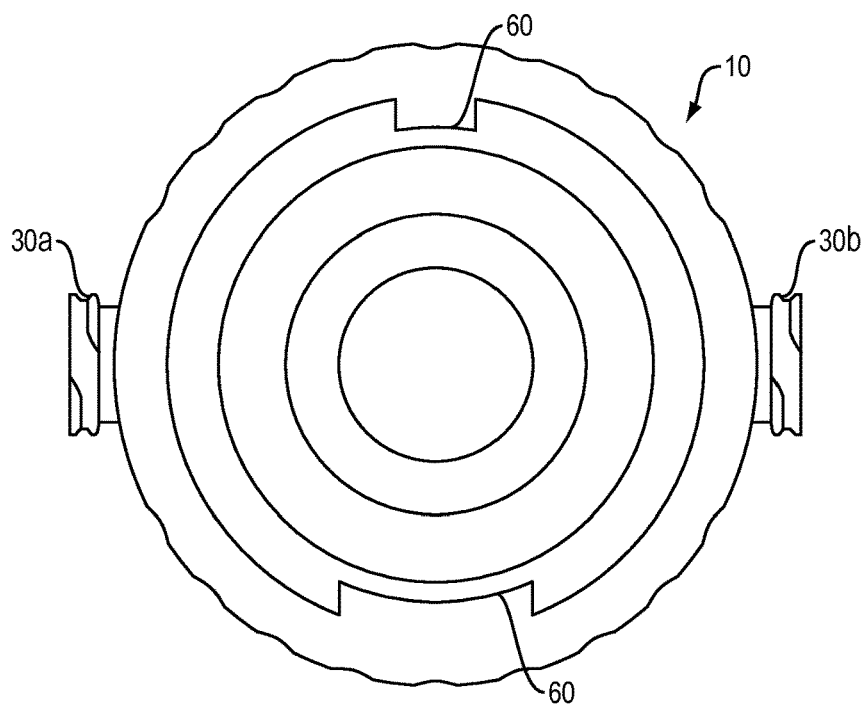
FIG. 12 is a front elevation view of at least a portion of the probe tip assembly.
Figure 13:
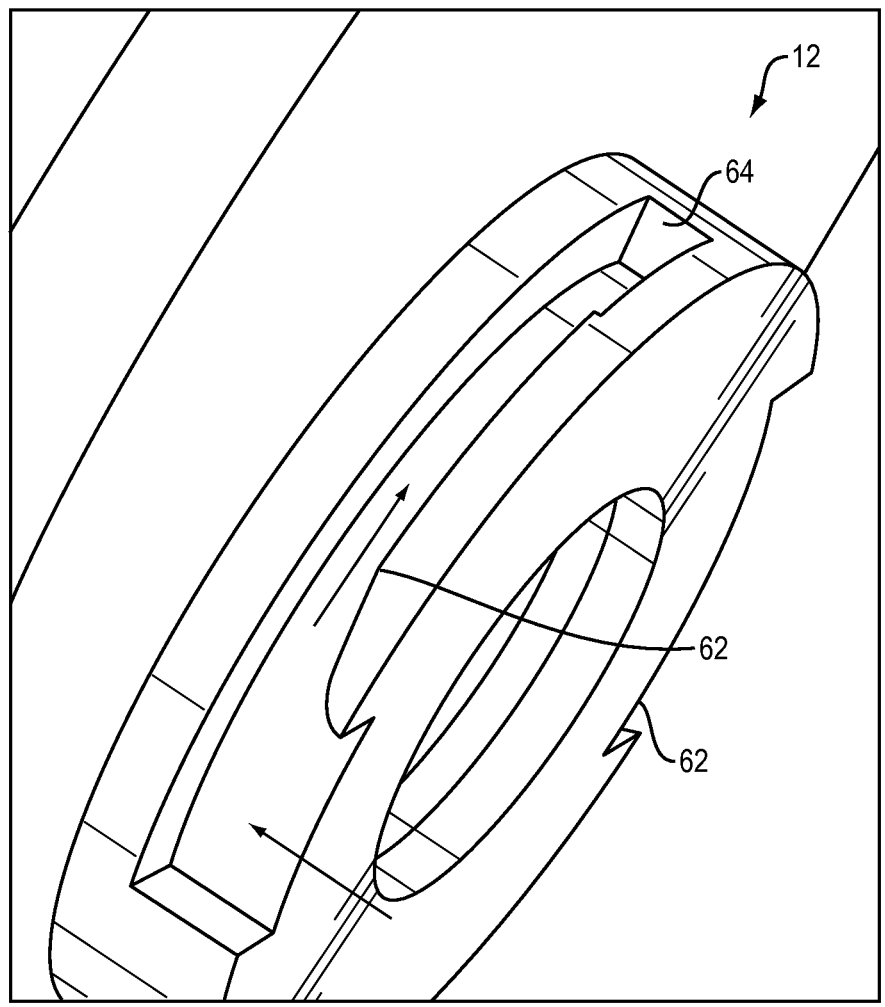
FIG. 13 is a perspective view of at least a portion of the probe.

For example, as shown in FIG. 12, the mechanism 28 may include one or more tabs 60. The tabs 60 may be diametrically opposed at or near the proximal end 22 of the probe tip assembly 28. The tabs 60 may or may not have an identical size, shape and/or configuration. For example, FIG. 12 shows two tabs 60 having a similar shape but a different size. One tab 60 may be exactly or approximately twice the size of the other tab 60. As shown in FIGS. 11 and 13, at least a portion of the probe 12, such as the probe housing 16 may include one or more undercuts 62. The undercuts 62 may be diametrically opposed at or near a distal end of the probe 12. The undercuts 62 may or may not have an identical size, shape and/or configuration. For example, FIGS. 11 and 13 show two undercuts having a similar shape but a different size. Each undercut 62 may be sized, shaped and/or configured to receive at least a portion of or an entirety of one of the tabs 60 therein. Each undercut 62 may be sized, shaped and/or configured to receive at least a portion or an entirety of only one (not both) of the tabs 60. As a result, the above-described mating geometries may allow only one correct orientation of the probe tip assembly 10 and the probe 12. Such features prevent at least a tip of the probe 12 from being placed in an incorrect or undesirable orientation within the probe tip assembly 10.

In one embodiment of the present disclosure, at least a portion of the mechanism 28 may be molded of an elastomeric USP Class VI polymer, may be sized and/or shaped such that it fits into, receives and/or is retained by at least a portion of the probe housing 16, which the probe tip assembly 10 will engage. At least a portion of the mechanism 28 may be used to create a wiper seal to or with the shaft 20 to eliminate fluid (e.g., water) ingress into the probe housing 16 internals, create a compression seal to the probe tip sealing surface in order to retain the fluid within the probe tip assembly 10; and act as a compression spring to force the probe tip assembly 10 to lock into locking grooves made or formed into the probe housing 16.

Figure 4:
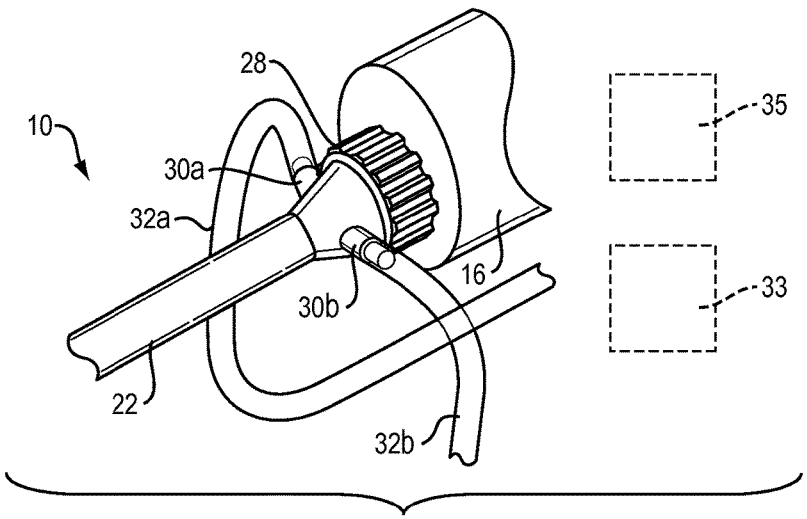
FIG. 4 is a perspective view of a portion of the probe tip assembly attached to a portion of the probe.

As shown in FIGS. 1 and 3-6, at least one or two or more ports 30a, 30b may be located at or near a proximal end of the probe tip assembly 10. One of the ports 30a, 30b may be an inlet port into the cavity of the probe tip assembly 10, and the other one of the ports 30a, 30b may be an outlet port from the cavity of the probe tip assembly 10. As shown in FIG. 4, each port 30a, 30b may connect to flexible tubing 32a, 32b. The tubing 32a, 32b, in turn, may be connected to a fixed or variable volume supply 33 (shown in broken lines in FIG. 4) of fluid, which may be degassed and bubble free, and which can be heated or cooled, and that can be pumped via a pump 35 (shown in broken lines in FIG. 4) under pressure into probe tip assembly 10.

Referring to FIG. 1, an air vent 34 may be located at or near the distal end 22b of the probe tip assembly 10. The air vent 34 can be in the form of a valve, a threaded screw, or any other means that can be manually or automatically opened and/or closed with ease and through which only air can flow, including Millipore filters and air only permeable membranes.

Figure 5:
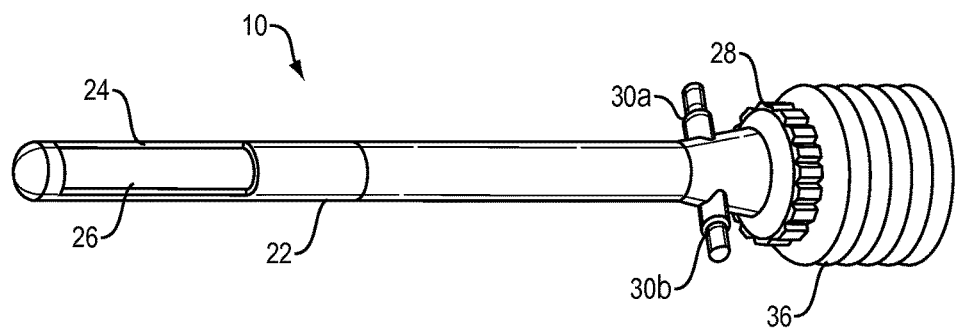
FIG. 5 is a perspective view of the probe tip assembly and at least a portion of a tube drape in a first configuration.
Figure 6:
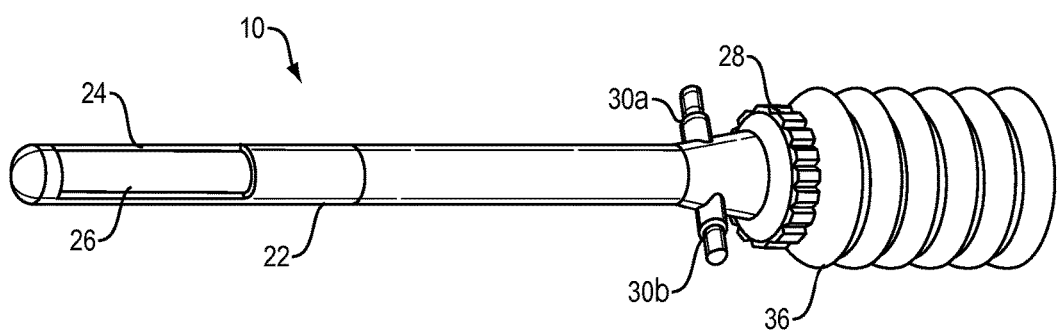
FIG. 6 is a perspective view of the probe tip assembly and at least a portion of the tube drape in a second configuration.
Figure 7:
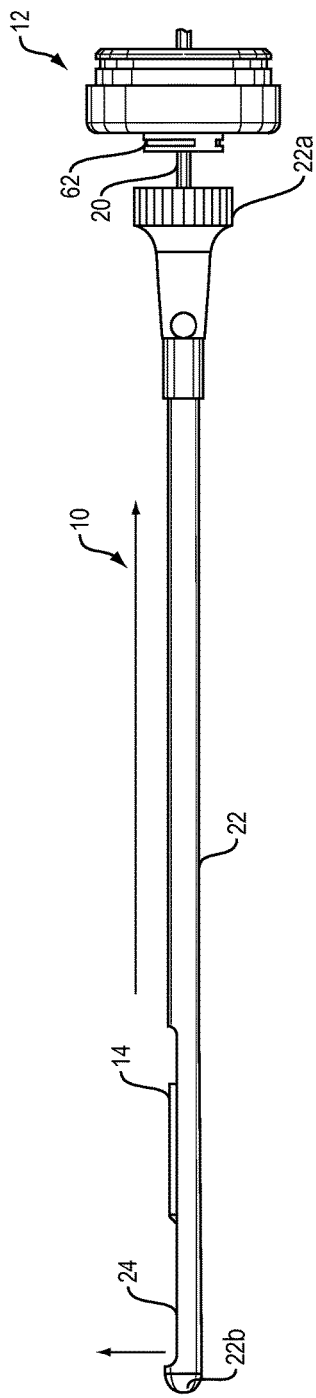
FIG. 7 is a side elevation view of the probe tip assembly and at a least a portion of the probe.
Figure 8:
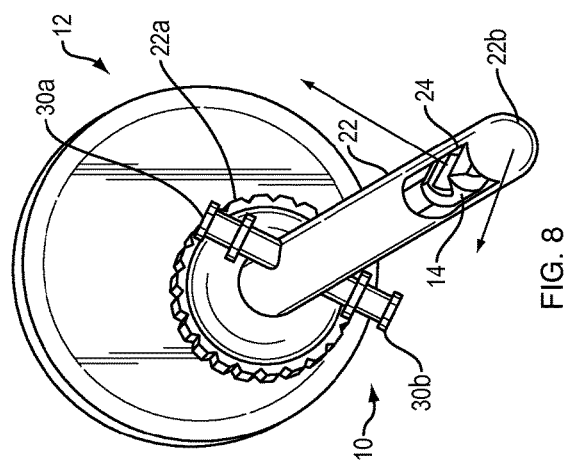
FIG. 8 is a perspective view of the probe tip assembly and at least a portion of the probe.

Referring to FIGS. 5 and 6, a compressible tube drape 36 may be secured to at least a portion of a most proximal end of the probe tip assembly 10. The tube drape 36 may be made of a material that is at least generally flexible, can be sterilized, and that is waterproof. The tube drape 36 may be used to cover at least a portion of or the entire probe housing 16 and may be attached to power and data cords in instances where the entire probe 12 needs to be used in a sterile field.

In operation, the probe tip assembly 10, which may be provided in a sterile or non-sterile package, may be unpackaged and placed over the ultrasound transducer 14 and at least a portion of or the entire shaft 20 of the probe 12. In order to engage at least a portion of the probe tip assembly 10 with or onto the probe housing 16, the probe tip assembly 10 may be slid over the exposed transducer 14 and shaft 20.

Figure 9:
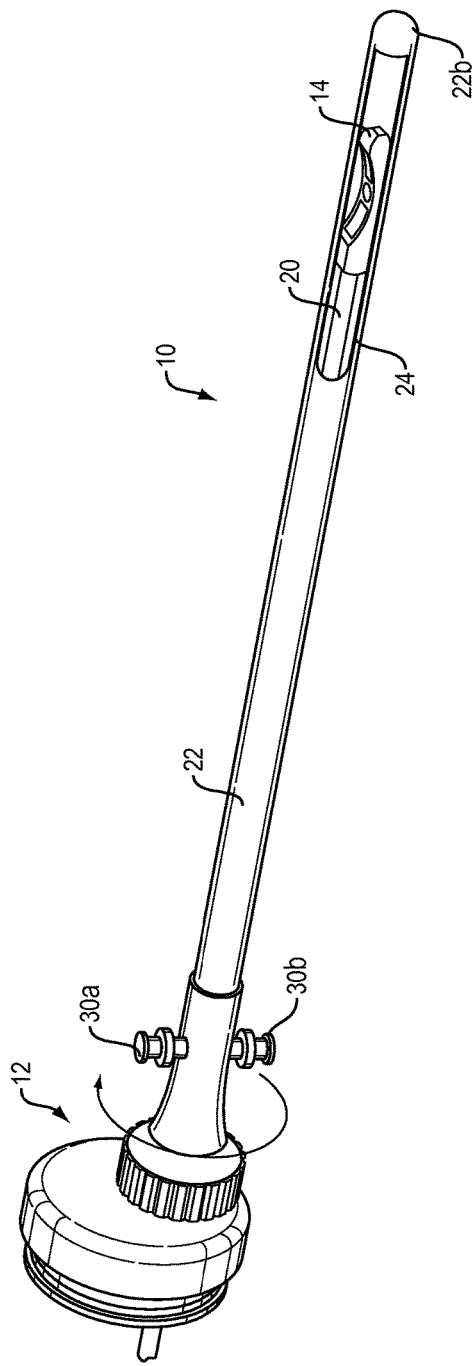
FIG. 9 is a perspective view of the probe tip assembly and at least a portion of the probe, wherein one of the probe tip assembly and the probe is being rotated to properly align at least a portion of a transducer to a window.
Figure 10:
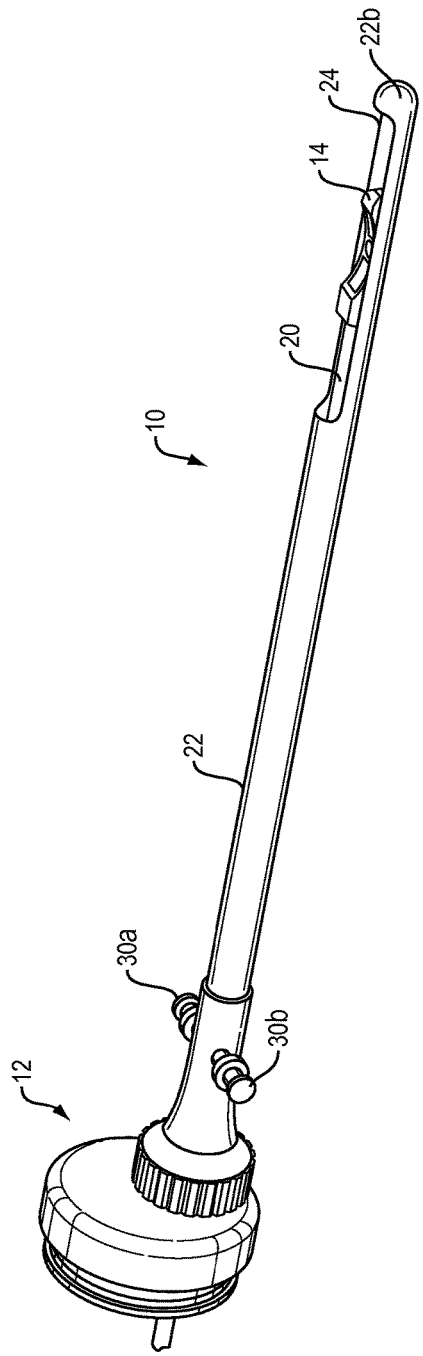
FIG. 10 is another perspective view of the probe tip assembly and at least a portion of the probe, wherein the transducer is properly aligned with the window.

One or more tabs 60 of the probe tip assembly 10 may be aligned with undercuts 62 on or in the probe 12. The tabs 60 may be inserted into the undercuts 62, and a force (e.g., a downward force) may be applied to at least a portion of the probe tip assembly 10 in order to compress the seal by about 30 to 40%, thereby allowing the tabs 60 to align with, contact or engage the undercuts 62. The probe tip assembly 10 may be rotated (e.g., clockwise) approximately 90 degrees until the tabs 60 are aligned with grooves 64 of the probe 12 (see FIGS. 9 and 13). The two arrows in FIG. 13 indicate at least one path one of the tabs 60 may travel within or relative to one of the undercuts 62.

When the probe tip assembly 10 is released from the probe 12, the seal forces each tab 60 into one of the grooves 64, such that the probe tip assembly 10 cannot be rotated accidently or during a procedure without or unless a significant compressive force is applied to the probe tip assembly 10 and seal initiating disengagement. To intentionally remove the probe tip assembly 10 from the probe 12, a force (e.g., a substantial downward compression force) may be applied to the probe tip assembly 10, allowing the tabs 60 to disengage from the grooves 64. The probe tip assembly 10 may then be rotated (e.g., counterclockwise) until the tabs 60 align with openings of the undercuts 62, at which time the probe tip assembly 10 may be slid up or out and over the shaft 20 and transducer 14 (see FIG. 7).

The above-described procedure aligns the probe tip assembly 10 correctly relative to the resting position of the transducer 14, so that the acoustic window 24 of the probe tip assembly 10 substantially or completely overlays the transducer 14. The tube drape 36, if provided, may be unrolled and brought down over the probe housing 16 and at least a portion of a power cable supplying the probe housing 16.

One end of each tubing 32a, 32b (or water lines) may be connected to one of the ports 30a, 30b of the tubing 32a, 32b, and an opposing end of each tubing 32a, 32b may be connected to the supply 33 of fluid, e.g., a reservoir containing degassed and bubble free water. The air vent 34 of the tubing 32a, 32b may be opened (e.g., partially or completely), the probe 12 may be held at least partially or completely vertical with the transducer 14 at a top thereof. Fluid circulation through the probe tip assembly 10 may begin by activating the pump 35 that is operationally connected to the fluid circulation system. As the fluid flows through one of the tubes 32a, 32b into the cavity of the probe tip assembly 10, the probe tip assembly 10 may begin to fill with fluid, thereby forcing air out of the vent 34. Once all or substantially all air is forced out and fluid begins to exit the vent 34, the vent 34 may be closed (manually or automatically, thereby creating a completely or substantially airless environment surrounding the transducer 14.

The distance between the transducer 14 and the coupling membrane 26 may be adjusted by the amount of additional fluid added into the probe tip assembly 10, which can be selectively controlled by the user. This distance can be used to ensure correct coupling between the probe tip assembly 10 and the tissue of the patient to be treated. It also can be used to adjust the distance of the transducer 14 from the tissue being treated, thereby allowing the distance to be optimized for the imaging or therapy procedure to be performed.

It will be appreciated by those skilled in the art that changes could be made to the embodiments described above without departing from the broad inventive concept thereof. For example, one or more of the features or components described as being part of the probe tip assembly 10 may form part of the probe 12. It is understood, therefore, that this disclosure is not limited to the particular embodiments disclosed, but it is intended to cover modifications within the spirit and scope of the present disclosure as defined by the appended claims.

We claim:

1. A probe tip assembly for receiving at least a portion of an ultrasound probe therein, the assembly comprising:
   a body defining a cavity and having a proximal end and an opposing distal end, the distal end defining a closed tip of the body, the closed tip having a convex exterior surface;
   a first opening at or near the proximal end of the body, the first opening being sized and shaped to receive at least a portion of an ultrasound probe therein;
   a second opening proximate the distal end of the body, the second opening having four spaced-apart corners, each corner having a radius of curvature;
   an acoustically transparent and distensible membrane covering the second opening, the membrane being bonded to the body;
   an inflow port extending outwardly at an angle from the body, the inflow port being spaced-apart from the proximal end of the body along a longitudinal axis thereof, the inflow port allowing fluid entry into the body cavity;
   an outflow port extending outwardly at an angle from the body, the outflow port being spaced-apart from the proximal end of the body along the longitudinal axis thereof, the outflow port being spaced-apart from the inflow port around an outer circumference of the body, the outflow port and the inflow portion being positioned at a common point along the longitudinal axis of the body, the outflow port allowing fluid passage from the body cavity, the outflow port being separated from the inflow port on an outer periphery of the body, the inflow and outflow ports being fluidly connected to a fluid supply system; and
   two diametrically opposed tabs at or near the proximal end of the body, each tab being configured to be inserted into an undercut of the ultrasound probe, one of the two tabs being larger than the other tab thereby permitting one correct orientation of the probe tip assembly and the ultrasound probe.

2. The assembly according to claim 1, wherein the assembly is disposable.

3. The assembly according to claim 1, further comprising:
   a tube drape connected to at least a portion of the proximal end of the body, the tube drape being distendable to cover at least a portion of the ultrasound probe after at least a portion of the ultrasound probe is inserted into the first opening of the body.

4. The assembly according to claim 1, wherein fluid is pumped into the assembly through the inflow port.

5. The assembly according to claim 1, wherein at least some air bubbles can be removed from the assembly through the outflow port.

6. The assembly according to claim 1, further comprising:
   a mechanism configured to secure at least a portion of the assembly to at least a portion of the ultrasound probe in an orientation that aligns the second opening with a transducer of the probe.

7. The assembly according to claim 1, further comprising:
   an air vent at or near the distal end of the body, the air vent being configured to be opened and closed.

8. The assembly according to claim 1, wherein a length of the second opening, as measured along the longitudinal axis of the body, is more than twice a length of a transducer of the ultrasound probe, as measured along a longitudinal axis of the ultrasound probe.

9. The assembly according to claim 8, wherein the transducer is not prevented from rotating within the body.

10. The assembly according to claim 8, wherein the transducer is located at a distal tip of the ultrasound probe, and wherein the ultrasound probe does not include a micromotor at the distal tip thereof.

11. The assembly according to claim 1, wherein the membrane is fluid impermeable.

12. A probe tip assembly for receiving at least a portion of an ultrasound probe therein, the assembly comprising:
   a body defining a cavity and having a proximal end and an opposing distal end, the distal end defining a closed tip of the body, the closed tip having a convex exterior surface;
   a first opening at or near the proximal end of the body, the first opening being sized and shaped to receive at least a portion of the an ultrasound probe therein;
   a second opening proximate the distal end of the body;
   an acoustically transparent and distensible membrane covering the second opening;
   an inflow port extending outwardly at an angle from the body, the inflow port being spaced-apart from the proximal end of the body along a longitudinal axis thereof, the inflow port allowing fluid entry into the body cavity;
   an outflow port extending outwardly at an angle from the body, the outflow port being spaced-apart from the proximal end of the body along the longitudinal axis thereof, the outflow port being spaced-apart from the inflow port around an outer circumference of the body, the outflow port and the inflow portion being positioned at a common point along the longitudinal axis of the body, the outflow port allowing fluid passage from the body cavity, the inflow and outflow ports being fluidly connected to a fluid supply system, and
   two diametrically opposed tabs at or near the proximal end of the body, each tab being configured to be inserted into an undercut of the ultrasound probe, one of the two tabs being larger than the other tab thereby permitting one correct orientation of the probe tip assembly and the ultrasound probe.

13. The assembly according to claim 12, further comprising:
   an air vent at or near the distal end of the body, the air vent being configured to be opened and closed.

14. The assembly according to claim 12, wherein the second opening has four spaced-apart corners, each corner being curved.

* * * * *